US008189044B2

(12) United States Patent
Stier (10) Patent No.: US 8,189,044 B2
(45) Date of Patent: May 29, 2012

(54) METHOD FOR OPTICAL INSPECTION OF A MATT SURFACE AND APPARATUS FOR APPLYING THIS METHOD

(75) Inventor: Oliver Stier, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 359 days.

(21) Appl. No.: 12/665,210

(22) PCT Filed: Jun. 16, 2008

(86) PCT No.: PCT/EP2008/057550
§ 371 (c)(1),
(2), (4) Date: Dec. 17, 2009

(87) PCT Pub. No.: WO2009/000689
PCT Pub. Date: Dec. 31, 2008

(65) Prior Publication Data
US 2010/0177191 A1 Jul. 15, 2010

(30) Foreign Application Priority Data
Jun. 22, 2007 (EP) .................................. 07075502

(51) Int. Cl.
*H04N 7/18* (2006.01)
*G06K 9/00* (2006.01)
(52) U.S. Cl. ..................... 348/92; 348/141; 348/E7.085
(58) Field of Classification Search .................... 348/92, 348/141, E7.085
See application file for complete search history.

(56) References Cited

U.S. PATENT DOCUMENTS

| 5,166,985 | A | 11/1992 | Takagi et al. ...................... 382/8 |
| 7,804,531 | B2 * | 9/2010 | DeLuca et al. ................ 348/241 |
| 7,847,840 | B2 * | 12/2010 | DeLuca et al. ................ 348/241 |
| 2007/0211242 | A1 | 9/2007 | Okabe et al. ............... 356/237.2 |
| 2008/0174678 | A1 * | 7/2008 | Solomon .................. 348/231.99 |
| 2010/0079974 | A1 * | 4/2010 | Kruger et al. ..................... 362/8 |
| 2010/0265324 | A1 * | 10/2010 | Spalding ........................ 348/92 |

FOREIGN PATENT DOCUMENTS
DE 4123916 1/1992
(Continued)

OTHER PUBLICATIONS

E. Deutschl et. al. "Defect Detection on Rail Surfaces by a Vision Based System", IEEE Intelligent Vehicles Symposium pp. 507-511: (6 Pages), Jun. 14, 2004.

(Continued)

*Primary Examiner* — Khanh Dinh
(74) *Attorney, Agent, or Firm* — King & Spalding L.L.P.

(57) ABSTRACT

In a method and apparatus for the optical inspection of a matt surface of an object, the surface having a random texture, for example a tile (11) to find cracks (12), in a first step digital images of the surface are created by an image sensor (K) whereby the surface is illuminated from different directions by light sources (B). In a second step sub-images of the regions of interest are created from the images. In a third step the cracks are detected in the sub-images by digital image processing, generating abnormality sub-charts showing the putative cracks. In a fourth step for each region of interest a joint abnormality chart is generated by fusion of the sub-charts and in a fifth step the cracks are detected in each of the joint abnormality charts of each region of interest.

14 Claims, 6 Drawing Sheets

FOREIGN PATENT DOCUMENTS

| | | |
|---|---|---|
| EP | 0452905 | 10/1991 |
| EP | 1832867 | 9/2007 |
| JP | 9311020 | 12/1997 |
| WO | 0010115 | 2/2000 |

OTHER PUBLICATIONS

Bonnot et. al. "Machine Vision System for Surface Inspection on Brushed Industrial Parts", Proceedings of SPIE-IS&T Electronic Imaging SPIE vol. 5303, 2004. pp. 64-72: (10 pages).

Pynn et. al. "Automatic Identification of Cracks in Road Surfaces", Image Processing and its Applications Conference Publication No. 465. IEE 1999. pp. 671-675 (6 pages).

International Search Report for Application No. PCT/EP2008/057550 (3 pages), Aug. 21, 2008.

European Search Report for Application No. EP 07075502 (5 pages), Jun. 5, 2008.

* cited by examiner

FIG 17

METHOD FOR OPTICAL INSPECTION OF A MATT SURFACE AND APPARATUS FOR APPLYING THIS METHOD

CROSS-REFERENCE TO RELATED APPLICATIONS

This application is a U.S. National Stage Application of International Application No. PCT/EP2008/057550 filed Jun. 16, 2008, which designates the United States of America, and claims priority to EP Application No. 07075502.0 filed Jun. 22, 2007, the contents of which are hereby incorporated by reference in their entirety.

TECHNICAL FIELD

The invention concerns a method for the optical inspection of a matt surface of an object, the surface having a random texture, for the purpose of finding texture anomalies.

BACKGROUND

Methods for optical inspections of surfaces in general are known from the state of the art.

E. Deutschl et al. describe in "Defect Detection on Rail Surfaces by a Vision based System", 2004, IEEE Intelligent Vehicles Symposium, pages 507 to 511, a method for optical inspections of rail surface defects. The inspection is performed by a simultaneous illumination of the rail surface with different light colours from different directions. This method, called spectral image differencing procedure, allows the automatic detection of defects on the rail surface. The method works because the metallic rail surface reflects light of all colours substantially to the same extent. N. Bonnot et al. disclose in "Machine vision system for surface inspection on brushed industrial parts", Proceedings of SPIE-IS&T Electronic Imaging, SPIE Vol. 5303, 2004, pages 64-72, a method for the inspection of reflecting surfaces to find surface defects like cracks. The inspection method includes an illumination procedure which uses two light sources illuminating the surface to be inspected from opposite directions at the same time.

J. Pynn et al. describe in "Automatic Identification of Cracks in Road Surfaces", Image Processing and its Applications, Conference Publication No. 465, IEE 1999, pages 671-675, a method which is able to detect cracks in the road surface by processing digital pictures taken of the road surface.

SUMMARY

According to various embodiments, a method for the inspection of surfaces can be created which is applicable to matt, randomly textured surfaces, and which is suitable for the detection of surface anomalies.

According to an embodiment, a method for the optical inspection of a matt surface of an object, wherein the surface has a random texture, for the purpose of finding texture anomalies, may comprise at least the following main steps: in a first main step n>1 digital images of the surface are created by an image sensor whereby the surface is illuminated from one direction for each image to be created whereby the directions for each image differ from each other; in a second main step r>0 regions of interest of the surface are defined whereby all regions of interest are entirely included in the n images and a matrix of n×r sub-images, which consist of the r regions of interest for each of the n images, is created; in a third main step texture anomalies are independently detected in the sub-images by digital image processing and n abnormality charts showing the putative anomalies for each sub image are generated; in a fourth main step for each of the r regions of interest a joint abnormality chart is generated by fusion of the n abnormality charts of said region of interest; and in a fifth main step texture anomalies are detected in each of the r joint abnormality charts.

According to a further embodiment, in an intermediate step brightness gradients in the n images or in the n×r sub-images resulting from the unidirectional illumination can be eliminated by an individual photometric normalisation of each of said images or sub-images, respectively, before the third main step. According to a further embodiment, in an intermediate step surfaces appearing in the n images or in the sub-images with curved boundaries can be transformed to shapes with straight or circular boundaries by an individual geometric normalisation before the third main step. According to a further embodiment, the third main step may comprise the following steps: in a first step a binary sub-image is created whereby connected pixels of the sub-image with a brightness and/or hue and/or saturation below or above a certain threshold are grouped into blobs; in a second step the blobs are analysed with respect to their size and/or their position on the surface and/or their spatial relation to each other. According to a further embodiment, the second step can be performed by a selection of relevant blobs which are defined by a minimal size, by a calculation of the distance matrix of the blobs and by a partition of the blobs based on their distances to find clusters of relevant blobs supposed to represent anomalies of interest. According to a further embodiment, the anomalies to be found can be cracks whereby linear, un-branched, open chains of relevant blobs are considered suspect. According to a further embodiment, there can be calculated by pixel fusion: all $q=n(n-1)/2$ possible sums of two out of the n images to generate q additional images before the second main step or all q×r possible sums of two out of the n sub-images belonging to the same region of interest to generate q×r additional sub-images for each region of interest before the third main step and that the q additional images, or the q×r additional sub-images, are treated identically as the n images or the n×r sub-images in all subsequent steps.

According to another embodiment, an apparatus for the optical inspection of the surface of an object may comprise a support frame which bears a camera and at least two light sources, the light sources and the camera being oriented towards the intended place for said surface, wherein the light sources can be driven separately by a controller.

According to a further embodiment, all light sources may emit light of the same spectrum. According to a further embodiment, the support frame may bear exactly four light sources.

BRIEF DESCRIPTION OF THE DRAWINGS

Further details of the invention can be found in the drawings where:

FIG. 9 shows a magnification of a blob from FIG. 8 whereby FIG. 9 is a cut out VIII of FIG. 8, FIGS. 15 and 16 present an alternative procedure for the detection of cracks by defining chips, whereby FIG. 15 represents the data matrix of the chips and FIG. 16 represents schematically an abnormality chart of outlier chips supposed to indicate a crack.

DETAILED DESCRIPTION

According to various embodiments, texture anomalies like cracks are found by performing at least the following main steps. In a first main step more than one (n>1) digital images of the surface are created by an image sensor whereby the surface is illuminated from different directions for each image to be created. In a second main step at least one, or more than one, (r>0) regions of interest of the surface are defined whereby all regions of interest are entirely shown in all of the n images. Subsequently a matrix of n×r sub-images is created which consists of the regions of interest in each of the n images. In a third main step texture anomalies are detected in the sub-images by digital image processing, and an abnormality chart showing the putative anomalies is generated for each sub-image. In a fourth main step for each of the regions of interest a joint abnormality chart is generated by fusion of all abnormality charts of that region of interest. In a fifth main step texture anomalies are detected in each of the joint abnormality charts.

The advantage of the proposed method is that, for the first time, the inspection of matt surfaces having a random texture can be performed with a high reliability. This reliability can be achieved by the combination of the said main steps according to various embodiments whereby the principal idea is the creation of a plurality of sub-images of one and the same region of interest, the sub-images differing by the illumination angle. These sub-images are interpreted separately by digital image processing to find putative texture anomalies. In this way abnormality charts of the texture anomalies can be generated which can be fused to a joint abnormality chart afterwards. In the joint abnormality chart the number of putative texture anomalies is reduced advantageously so that the detection rate for true texture anomalies like cracks can be enhanced to a percentage close to 100% at a very small false alarm rate.

According to an embodiment, in an intermediate step brightness gradients in the n images, or in the n×r sub-images, as resulting from the unidirectional illumination are eliminated by an individual photometric normalization preceding the third main step. This intermediate step enhances the results of the digital image processing in the third main step if there are brightness gradients across the images (sub-images) due to a narrow emission area of the light sources. In this case a photometric normalization results in that a given texture anomaly will yield essentially the same brightness modulation regardless of its location in the sub-image or image. The photometric normalization can be performed before or after the creation of sub-images from the images.

According to an embodiment, in an intermediate step surfaces appearing with curved boundaries in the n images or in the n×r sub-images are transformed to elementary shapes with, e.g., straight or circular boundaries by an individual geometric normalization before the third main step. Such a reduction of general shapes to elementary ones helps advantageously to reduce the computational expense of the later image processing.

According to an embodiment, the third main step comprises the following steps. In a first step a binary sub-image is created whereby all pixels of the sub-image with a brightness (B) and/or hue (H) and/or saturation (S) below, or above, a certain threshold are grouped to blobs. In a second step the blobs are analysed according to their size and/or their position on the surface and/or their spatial relation to each other. The thresholds have to be determined depending on what texture anomalies are to be found. To find the optimal thresholds for a given application empirical values have to be determined from a number of test measurements. Thus thresholds can be found yielding blobs bearing the information on all putative texture anomalies. Depending on the application, thresholds for one or more of the attributes brightness (B), hue (H) and saturation (S) have to be found. A thresholding like that is based on the commonly known HSB-color-model.

To filter the relevance of the blobs further properties can be analysed, e.g., the size of the blobs, their position on the surface, or their spatial relation to each other. The results of the analysis can be compared to known properties of the texture anomalies to be found. Irrelevant blobs are discarded before the next step.

A further refinement of the first main step is that its second step comprises the following steps: A selection of relevant blobs identified by a minimal size, a pairwise calculation of a distance between all blobs, and a partitioning cluster analysis based on that distance function to find clusters of relevant blobs suspect to form an anomaly. This procedure advantageously reduces the number of actually irrelevant blobs having been marked erroneously by the thresholding. The idea behind this refinement is that eventually such blobs remain relevant which have a minimal size and are separated from other blobs by a maximal distance. These blobs can be combined to clusters which represent an anomaly more likely than isolated blobs. Advantageously, cracks can be found easily this way whereby linear, unbranched, open chains of relevant blobs are considered suspect clusters.

The reliability of the method can be further improved if all q possible sums of two out of the n images are calculated by pixel fusion to generate q additional images before the second main step, or if all q×r possible sums of two out of the n sub-images belonging to the same region of interest are calculated to generate q×r additional sub-images for each region of interest before the third main step. These q additional images or q×r additional sub-images are treated identically as the n images, or the n×r sub-images, in all subsequent steps.

According to yet another embodiment, an apparatus for the optical inspection of the surface of an object comprises a support frame which bears a camera and at least two light sources whereby the light sources and the camera are oriented towards the place intended for said surface. This place could be a carrier for the object which also is integrated in the support frame. The camera and the light sources might as well be oriented towards the base of the support frame whereby the support frame base can be positioned on the surface to be inspected.

According to this embodiment an apparatus for the optical inspection of surfaces can be provided which allows to use the method for the optical inspection quickly and reliably.

For this purpose the apparatus according to various embodiments comprises a plurality of light sources which can be driven separately by a controller. This is advantageous because the above described method can be run on the apparatus whereby the plurality of images under different illumination angles can be taken without changing the position of the support frame or the position of the light sources attached to the support frame. Advantageously, the method can be run after one single adjustment step of the apparatus, saving time and gaining accuracy.

If all light sources emit light of the same spectrum a photometric normalization can advantageously be performed in an easy way. Furthermore, surfaces with colours changing along the area can easily be inspected.

In a special refinement of the apparatus the support frame bears exactly four light sources forming the corners of a rectangle similar to and equally oriented as the boundary of rectangular objects under inspection. For example, wall tiles of combustion chambers have an approximately rectangular shape. The method and the apparatus having four light sources are particularly appropriate for finding cracks in the tile surface.

Alternatively also gas turbine or compressor blades can be inspected by the method according to various embodiments. Gas turbine blades comprise different coatings which appear matt and with a random surface texture. The method for the inspection of gas turbine blades could be applied to a quality control after production to find e.g. cracks. The method could also be applied to the inspection of worn turbine blades after a certain operating time whereby the progress in abrasion or corrosion of the coatings on the turbine blades can be evaluated. Also cracks in the surface of the coatings can be detected. This applies analogously to compressor blades.

The following description refers to the optical inspection of a wall tile 11 for use in a combustion chamber of a gas turbine. This is only an example and does not restrict the scope of the invention to this application case.

Figure 1:
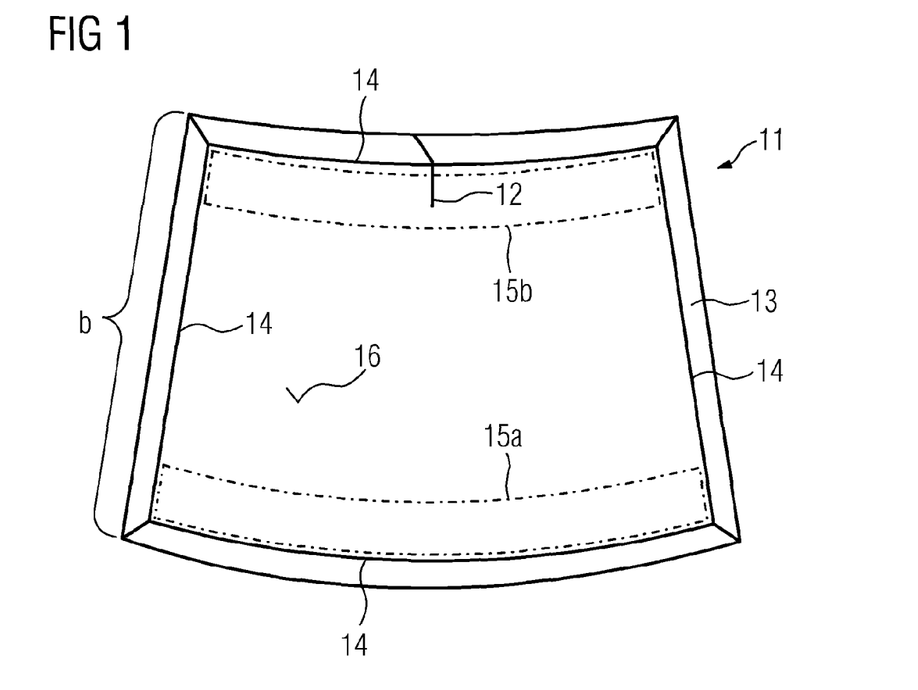
FIG. 1 shows a plan view of a wall tile from a combustion chamber as object to be inspected.

A wall tile 11 is shown in FIG. 1. As a matter of experience in the visual inspection of such wall tiles, cracks in the surface 16 are very hard to find if the illumination is not optimal. In the wall tile 11 for example a crack 12 shall be found by the method of inspection according to various embodiments. For that purpose according to the method according to various embodiments a number of images are taken of the surface 16 under different illumination angles (i.e. from each corner of the wall tile 11). These images will, at first, be analyzed individually in the following steps of the method according to various embodiments. For a better understanding these steps carry numbered headlines (V1, V1.1.1 . . . V4), whereby for certain steps V alternative steps W are presented, indicating their correspondence by using same numbers.

Instead of a wall tile any other object with a matt and random textured surface can be inspected.

V1.1 Registration of the Object (Finding the Boundary)

The tile boundary can be localized by known methods for edge detection, morphological segmentation, etc., and be reconstructed to an idealized, continuous shape by known methods of geometrical data processing, like interpolation. These methods will make ample use of any available a priori information on the object shape and its position within the given environment, taking into account CAD models and similar means. In the given example, the tile 11 has a bevel 13 whose interior edge defines the relevant object boundary 14.

V1.2.1 Isolation of the Object by Hiding the Surroundings

All pixels outside the boundary 14 are deleted, i.e. the mask frame 14 of the wall tile 11 is defined by the interior edge of bevel 13.

V1.2.2 Segmentation of the surface image into r regions of interest (RoI)

In the chosen example of the wall tile 11 only cracks are interesting texture anomalies to be found. Furthermore, the cracks are supposed to extend from the tile boundary to its inner region. Therefore the regions of interest 15a, 15b are defined. The width of the defined regions of interest 15a, 15b is ⅙ of their length since it is presumed that mechanically relevant cracks have a minimal length in the order of magnitude of this width.

V1.2.3 Creation of r Selection Masks (One for Each RoI)

For each region of interest a separate mask is generated analogous to V1.2.1 including the relevant pixels and hiding all pixels which do not belong to that region of interest.

By means of these selection masks all regions of interest are extracted from each sub-image. The overall result is a set of n×r sub-images of the regions of interest of the object.

V1.3 Individual Photometric Normalization of the n×r Sub-Images (Images)

Figure 2:
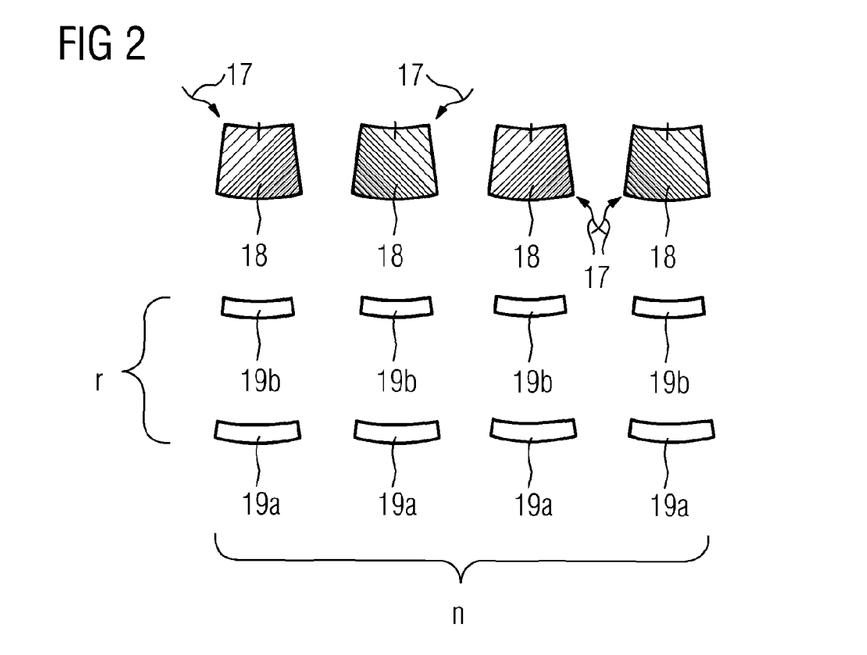
FIG. 2 shows n images of the wall tile from FIG. 1 and n×r sub-images of the r regions of interest indicated in FIG. 1.

By the nature of the proposed method, the various single sub-images (this method also applies to the images entering V1.1, though not explicitly described in the following) of one region of interest 15a, 15b differ strongly in their spatial illumination profiles, and each exhibit large brightness gradients, as can be seen schematically by the hatched surface 16 of the tile 11 in FIG. 2. The tile is illuminated sequentially from four different directions 17 yielding the shown illumination profiles. For each illumination direction one image 18 is taken (n=4). From each image 18 two sub-images corresponding to the RoI 15a, 15b are extracted (r=2). This means that n×r=8 sub images will have to be analysed. The different illumination profiles prevent, on the one hand, reasonable results from superposing such images as in V1.6 and, on the other hand, render thresholding procedures as in V1.7.1 fruitless. Therefore an individual photometric normalization is prerequisite here for the further processing. The first step of the normalization is the compensation of the camera gradation, i.e., the translation of the generic gray scale image into an intensity image. The second step is the arithmetic decomposition of the intensity image into two layers, the pixel-wise superposition of which returns the intensity image. The first layer is the spatial brightness profile the body surface would yield in absence of its texture, as a result only of the angular intensity distribution of the light source, the overall curvature of the body surface and its diffuse and, if applicable, specular reflectivity. The second layer is the intensity image the body surface would yield after hypothetical planarization, and under perfect unidirectional, homogeneous illumination, as a result only of its texture relief. This layer is selected for further processing, the first layer being dropped. The third and last step of the normalization is a transformation of the (second layer) pixel values such that the main part of the intensity distribution (without outliers) will approximately obey a standard normal distribution.

Figure 3:
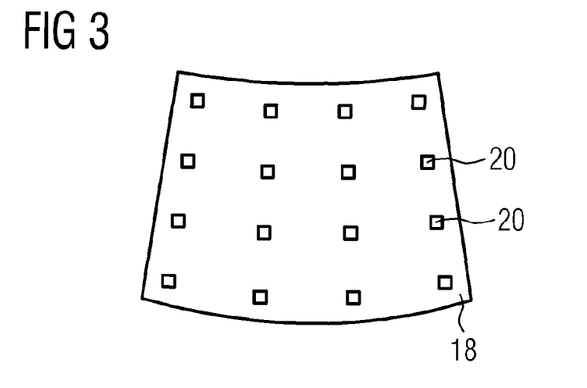
FIG. 3 shows an example of that step of the inventive method which contains the photometric normalization of the n images.
Figure 4:
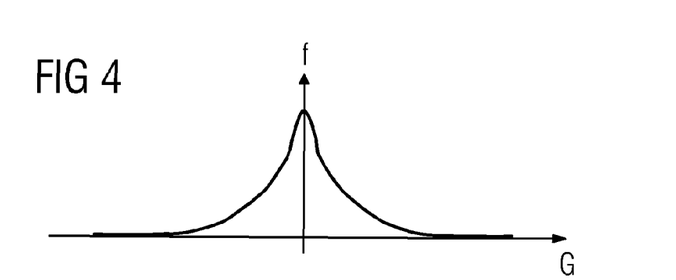
FIG. 4 shows a histogram of the brightness (B) distribution resulting from the photometric normalization of the image in FIG. 3, FIGS. 5 and 6 show smoothed contour plots of the autocorrelation functions of two images of two different tiles to estimate and distinguish the respective degrees of body surface decomposition.

The normalization procedure is visualized in FIGS. 3 and 4. To construct the first layer (the global intensity profile)

from the intensity image shown in FIG. 3 the latter is sampled by a certain number of chips 20 in the manner of an exposure meter. The tiny sub-images within the chips 20 are analyzed by procedure W1.7.2 to W1.7.4 to reject unrepresentative chips. The average intensities of the accepted chips are used as data points to extract the continuous global intensity profile from the image. In this example, the global intensity profile was calculated by assuming a five-parameter ellipsoid shape of the tile surface 16, a point light source with a three-parameter angular intensity profile and the Blinn-Phong shading model including diffuse and specular reflection. Including the positions of light source and camera, this shading model has 17 parameters for which maximum likelihood estimates were calculated from 58 data points using a derandomized (1,10)-evolution strategy with correlated mutations and individual step size.

The second layer is the fit residual, i.e. was calculated by subtracting the global profile (first layer) from the original intensity image. Finally, the pixel intensity values in the fit residual are transformed to approximately unit variance (the median of the residual of a correct fit is already zero). The resulting histogram (pixel brightness B on x-axis and frequency on y-axis) is shown in FIG. 4.

To handle other body shapes and illumination characteristics the shading model can be adapted appropriately. Thus, the proposed photometric normalization procedure is by no means restricted to images of wall tiles from turbine combustion chambers.

V1.4 Optional Individual Geometric Normalization of the n×r Sub-Images (or Images Entering V1.1, Though not Explicitly Described in the Following)

For convenience of the subsequent data handling the typically irregularly shaped regions of interest (or the whole tile) are smoothly transformed to elementary shapes, e.g., rectangles. It is advantageous to maintain the original pixel structure to an as large as possible extent, to avoid distortion artifacts in V1.7.2 to V1.7.6. An appropriate transformation of the two regions of interest (RoI) 15a, 15b shown in FIG. 1 to rectangles can be performed by pixel column shifts.

V1.5 Estimate for the Degree of Body Surface Decomposition (Optional)

Figure 5:
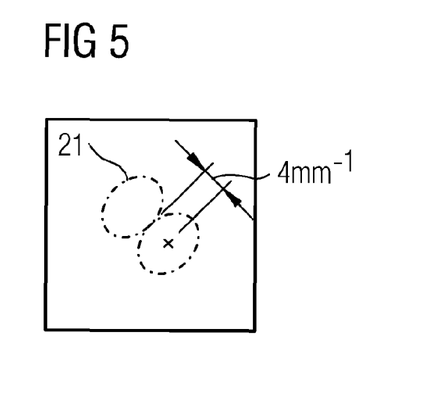
Figure 6:
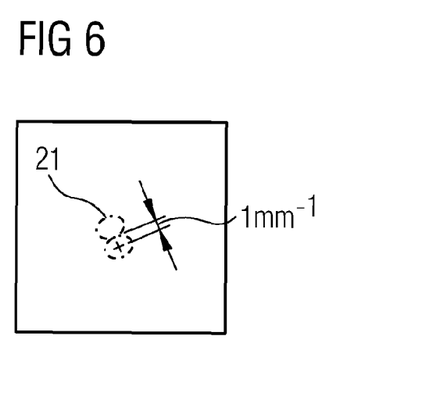

Due to varying exposures to erosion or corrosion the body surfaces to be inspected can exhibit strongly varying degrees of structural decomposition. The degree of surface decomposition is an additional global characteristic of the surface texture and not only of interest per se, but can also be considered when selecting threshold values and pass bounds for the various processing steps in V1.7. An advantageous choice to quantify the surface decomposition is the average feature size measured in either (i) a defect free region, (ii) a typical region, or (iii) throughout the entire visible region of the body surface. Whatever region chosen, the average feature size is advantageously calculated from the image autocorrelation function, shown schematically as contour plots in FIGS. 5 and 6. The butterfly shape of the autocorrelation function 21 visualizes the preference of feature orientation due to the unidirectional illumination. The reciprocal of the weighted average of the spatial frequency modulus is the average feature size. The typical feature sizes obtained in this application example are 1 mm for new, defect free tiles (FIG. 5) and 4 mm for structurally decomposed tile (FIG. 6).

V1.6 Creation of q×r Additional Sub-Images (or Alternatively q Additional Images which is not Described in the Following) For Each Region of Interest Using Pixel Fusion Pixel-wise arithmetic combinations (e.g. addition) of the normalized sub-mages of one and the same region of interest can enhance the appearance of surface defects. Due to the opposite positions of the light source during the two respective exposures shadow and light on many random features cancel to significant extent while the crack 12 is unaffected, due to its accidental orientation with respect to the light source shift. Hence, the contrast of the crack 12 becomes larger than in the parent sub-images. The appreciable extent of cancellation is the result of the preceding photometric normalization due to V1.3. Without V1.3, a systematic cancellation of irrelevance could not have been expected. Since, in the general case, it is not known a priori which orientations the wanted surface defects will have, one does not know in advance which combinations of original images will yield the maximal enhancement of the wanted defect. Hence, according to various embodiments it is proposed to calculate all $$q = \binom{n}{2} = \frac{n(n-1)}{2}$$

possible sums of two out of the n original (normalized) sub-images, yielding q×r additional sub-images in total. Arbitrary linear combinations of the n original sub-images might be added, loosely corresponding to illumination from multiple light sources of different (even negative) intensities. For this, as well as other applications than searching for surface cracks in turbine combustion chamber wall tiles, other pixel-wise image fusions, including multiple or stacked fusions, can readily be substituted, as appropriate. The newly created q×r sub-images are unified with the n original images of the given region of interest and handled as one set in the following.

V1.7 Detection of Crack-Like Texture Anomalies in Each of the (n+q)×r Sub-Images The method according to various embodiments is based on the two findings that (i) under appropriate illumination a crack in a bright textured surface is visible by the appearance of dark pixels forming characteristic spatial patterns, and that (ii) among these dark pixels a significant number are exceptionally dark, i.e., are outliers from the approximate standard normal distribution of brightness values obtained as a result of V1.3 and shown in FIG. 4. Hence, method V1.7 commences with the isolation of the darkest pixels prevailing in the sub-image, and is accomplished by a comprehensive analysis of their spatial connectivity.

V1.7.1 Creation of Binary Images by Thresholding of the Sub-Images

A fraction f is chosen, either by prescription or auto-thresholding, and the f-quantile of the brightness distribution in the given sub-image calculated. The quantile is chosen as a threshold, and all pixels with brightness values below the threshold are selected. These are called foreground pixels, and all pixels not selected are called background pixels.

Figure 7:
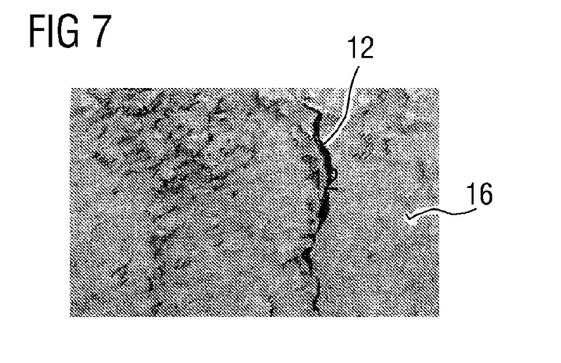
FIGS. 7 and 8 present one example of a sub-image of the wall tile from FIG. 1 before and after respectively, the creation of a binary image by thresholding.
Figure 8:
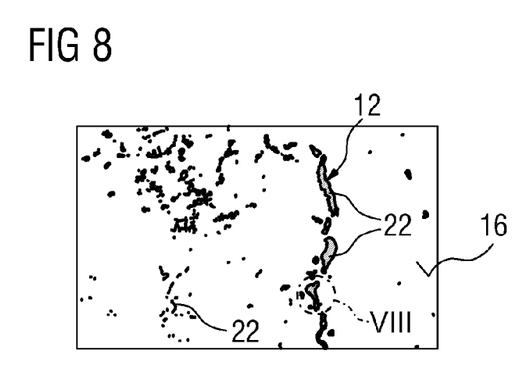

FIGS. 7 and 8 show the effect of this process. The submitted sub-image is shown in FIG. 7. Apart from the normalization according to V1.3 and V1.4, this is an original photograph. This sub-image is decomposed by the 1%-quantile, yielding the binary image shown in FIG. 8.

V1.7.2 Grouping the Foreground Pixels into Blobs

Figure 9:
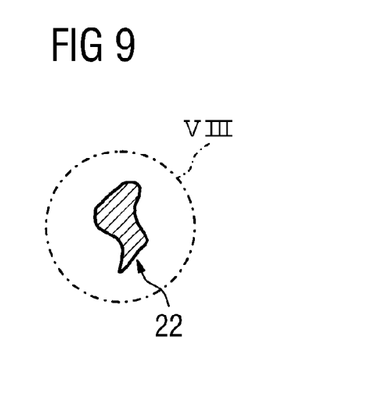

A rectangular foreground pixel is called a boundary pixel if, and only if, it shares an edge with at least one background pixel. All foreground pixels not being boundary pixels are called interior pixels. FIG. 9 shows the partition of an enlarged part VIII of FIG. 8 into interior (hatched), boundary (black), and background (white) pixels. Two rectangular pixels are said to be adjacent if, and only if, they share a common edge or corner. A blob is, by definition, a set of foreground pixels which contains all pixels adjacent to a pixel p if, and only if, it contains the pixel p. There is a unique partition of the set of all foreground pixels into blobs 22. The blobs 22 are separated by background pixels. The construction of the blobs 22 from a given binary image is accomplished by known iterative-recursive algorithms. In what follows, only the blobs 22 will be considered, while the background pixels are discarded.

V1.7.3 Selection of Relevant Blobs

Figure 10:
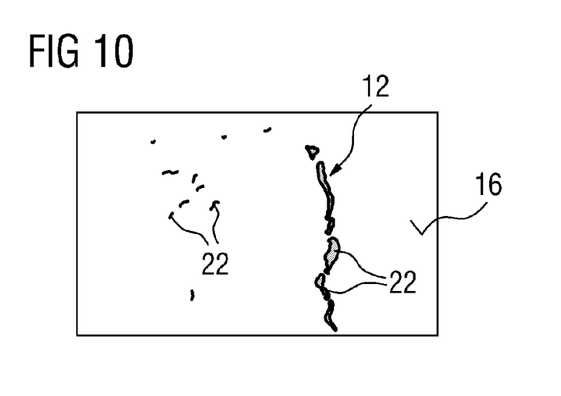
FIG. 10 shows the sub-image from FIG. 8 after the reduction to relevant blobs.

According to various embodiments, all blobs smaller than a specified size are dropped. The size of a blob 22 is measured here by the blob diameter d, defined as the maximal Euclidian distance existing between any two pixels of the blob. For the calculation of the blob diameter d only the boundary pixels are necessary. FIG. 10 shows all blobs from FIG. 8 having a diameter of at least 15 pixel units. The largest blob has a diameter of 70 pixel units.

For other applications than searching for surface cracks 12 in turbine combustion chamber wall tiles different size measures or selection criteria can be defined, as appropriate. It is advantageous, at least, to define all metric quantities related to blobs in a way that they can be calculated from the boundary pixels only, as is the case for the blob diameter, as well as for the blob distance introduced below. This, together with the selection of a small subset of relevant blobs, results in appreciable savings of computational expense.

V1.7.4 Calculation of the Blob Distance Matrix

The most important ingredient to the single sub-image evaluation procedure V1 is the adequate choice of a distance function between blobs 22. The subsequent partition, or grouping, respectively, of the blobs in V.1.7.5 will be based on a calculated adjacency criterion which is derived from the blob distance matrix defined here. At this instance, one assumption about the topological structure of a crack is made which has some effect on the present choice of the distance function and is specific to surface cracks in ceramic wall tiles for turbine combustion chambers, but can easily be modified for a detection of cracks in other brittle body surfaces. The assumption made here is that the connection topology of a crack is necessarily a linear, open chain of blobs containing no branching. Such a chain either consists of one blob 22 only, or contains exactly two blobs 22 having one nearest neighbor only while all other blobs 22 have exactly two nearest neighbors. This definition determines the target adjacency structure used in V1.7.5 and motivates the construction of the distance function as proposed below. The present definition of the distance function intentionally avoids assumptions about geometrical properties of the blobs 22, and proves useful in this general form. For other applications than searching for surface cracks in turbine combustion chamber wall tiles geometrical requirements can readily be incorporated to the distance function, as appropriate.

The single linkage distance $s_{ij}$ between two blobs i and j is known as the shortest Euclidian distance existing between a pixel in blob i and a pixel in blob j. $s_{ij}=0$ if, and only if, one pixel of blob i is adjacent or identical to a pixel in blob j, then the blobs i and j are identical. $s_{ij}$ is calculated from the boundary pixels only. The application specific distance $\alpha_{ij}$ between two blobs i and j according to various embodiments involves a direction (or orientation) parameter $\delta$, $0<\delta\leq 1$, and a spacing parameter $\sigma$, $0\leq\sigma<1$, such that by definition $\delta\to 1$ for $\sigma\to 1$. For $s_{ij}\to 0$, by definition $\sigma\to 0$. $\sigma=0$ if, and only if, $s_{ij}=0$. For $s_{ij}\to\infty$, by definition $\sigma\to 1$. By definition, $\delta=1$ indicates an optimal alignment of the two blobs at given spacing, and $\delta$ becomes the smaller, the less favorable the alignment of blob i towards blob j is in terms of the application specific expectations. In the case of blobs 22 suspected to from a crack 12 in the surface 16 of a turbine combustion chamber wall tile 11, we choose $\delta=1$ if, and only if, the line segments visualizing the blob diameters $d_i$ and $d_j$ of the two blobs lie on the same line, i.e., if one blob is a straight continuation of the other (realizing the equality case of the triangle inequality), and furthermore choose $\delta$ to decrease significantly if the two blobs, e.g., form a sharp angle, a T-shape junction, or are aligned parallel. From these two parameters, $\delta$ and $\sigma$, the distance $\alpha_{ij}$ according to various embodiments is defined such that $\alpha_{ij}=0$ if, and only if, $\sigma=0$, that $\partial\alpha_{ij}/\partial\sigma>0$ for $0\leq\sigma<1$ with $\alpha_{ij}\to\infty$ for $\sigma\to 1$, and that $\partial\alpha_{ij}/\partial\delta<0$ for $\sigma\to 0$, each for $0<\delta\leq 1$. According choices for $\alpha_{ij}$ are, e.g., $$a_{ij} = \tan\left(\frac{\pi}{2}\sigma^\delta\right)$$

or $$a_{ij} = \left[\tan\left(\frac{\pi}{2}\sigma\right)\right]^\delta.$$

The latter expression reduces the influence of $\delta$ as compared to the first and has been used throughout the examples presented here. Advantageous choices for $\delta$ and $\sigma$ avoiding assumptions about the geometrical blob shapes are, e.g., $$\delta_{ij} = \frac{d_{ij}}{d_i + d_j + s_{ij}}$$

and $$\sigma_{ij} = \frac{s_{ij}}{d_{ij}}$$

where $d_{ij}$ is the blob diameter of the pixel union of the blobs i and j, i.e., the largest Euclidian distance existing between any two pixels from the blobs i and j. With k being the number of blobs selected in V1.7.3 the distance matrix $$(\alpha_{ij}) \text{ for } i,j=1\ldots k$$

is symmetric with a vanishing diagonal, but not containing zero elements elsewhere.

V1.7.5 Partitioning Cluster Analysis of the Blobs

The topological characteristics of a surface crack 12 in a turbine combustion chamber wall tile 11 assumed above are translated into an adjacency matrix according to various embodiments as follows. Define the set $m_i$ containing two elements by sorting the k−1 values of $$\{\alpha_{ij}|j\neq i\}$$

in ascending order and taking the first two elements of that ordered set. Then the adjacency matrix A is the symmetric rank k matrix with the matrix elements $$a_{ij} = \begin{cases} 1 & \text{if } (i\neq j)\wedge(a_{ij}\in m_i)\wedge(a_{ij}\in m_j) \\ 0 & \text{otherwise.} \end{cases}$$

Thus, two blobs i and j are considered adjacent if, and only if, they are mutual nearest or second-nearest neighbors in terms of the distance function defined in V1.7.4. In most cases a blob 22 will be adjacent to, at most, two other blobs 22, multiple adjacencies will occur accidentally, and many blobs 22 will be isolated, i.e., not be adjacent to any other blob. The present definition of A directly reflects the above assumption of a crack manifesting itself as a linear, unbranched, open blob chain 23. For other applications than searching for surface cracks 12 in turbine combustion chamber wall tiles 11 different adjacency criteria can readily be defined, as appropriate.

Figure 11:
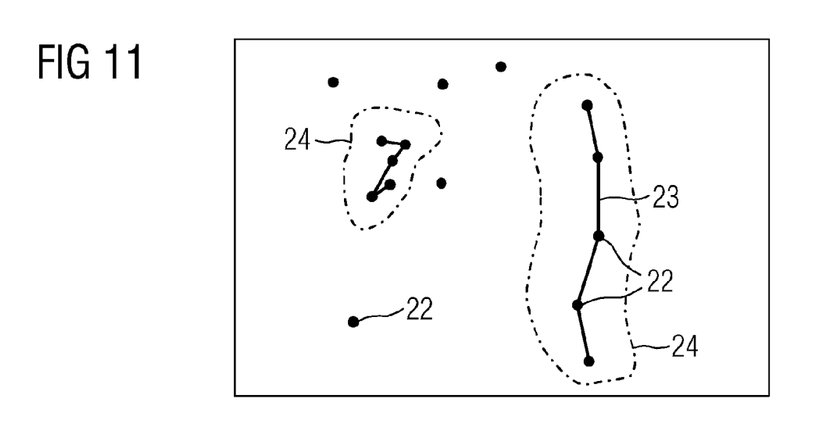
FIG. 11 shows the embedding of the calculated adjacency graph of the sub-image from FIG. 10.

A corresponds to an undirected, unweighted graph which, in the general case, is disconnected. The connected components of that graph are disjunct sets of adjacent blobs 22, called blob clusters 24, and represent a unique partition of the adjacency graph. FIG. 11 shows an embedding of the adjacency graph resulting from the blob selection shown in FIG. 10, using the blob centroids as vertex coordinates. Adjacent blobs (connected vertices) are indicated by connecting lines. This partition yields seven clusters, five of which contain isolated blobs, and two of which contain more than one blob.

V1.7.6 Selection of Suspect Blob Clusters

From the clusters 24 found in V1.7.5 those are selected which are likely to represent cracks 12 in the turbine combustion chamber wall tile 11 surface. Again, the selection criteria presented here can easily be adapted to other applications, in particular geometric criteria can be used, which intentionally are omitted here. The first criterion for a suspect cluster is that its blobs form a linear, unbranched, open chain. Second, advantageous parameters apt to the first-level discrimination of false detections are obtained from generalizing the above introduced parameters $d_{ij}$, $\delta_{ij}$, and $\sigma_{ij}$ to blob clusters of arbitrary size c, with c being the number of blobs forming the cluster. This is possible by converting the adjacency graph corresponding to a cluster into a weighted graph. The weight assigned to an edge is chosen as the single-linkage distance $s_{ij}$ between the blobs corresponding to the two vertices i and j terminating the edge. Define $d_{1c}$ as the blob diameter of the pixel union over the entire blob cluster, and $s_{1c}$ as the weight of the minimal spanning tree of the weighted adjacency graph of the cluster. Then, by definition $$\delta_{1c} = \frac{d_{1c}}{s_{1c} + \sum_{i=1}^{c} d_i}$$

and $$\sigma_{1c} = \frac{s_{1c}}{d_{1c}}.$$

According to various embodiments, such clusters 24 passing the above, topological chain criterion are considered suspect whose parameters $d_{1c}$, $\delta_{1c}$, and $\sigma_{1c}$ lie in certain, specified intervals (which can be open). A typical choice is the specification of lower bounds for $d_{1c}$ and $\delta_{1c}$ and an upper bound for $\sigma_{1c}$. Application of these criteria discriminates, e.g., the left cluster shown in FIG. 11 as harmless ($\delta_{1c}$ is too small), while classifying the right cluster shown in FIG. 11 as a potential crack 12.

Along with the possible definition of other selection parameters for different applications, other Boolean functions than the logical product of interval memberships can easily be defined for classifying the computed clusters, as well.

V1.7.7 Abnormality Chart Displaying Putative Cracks

Figure 12:
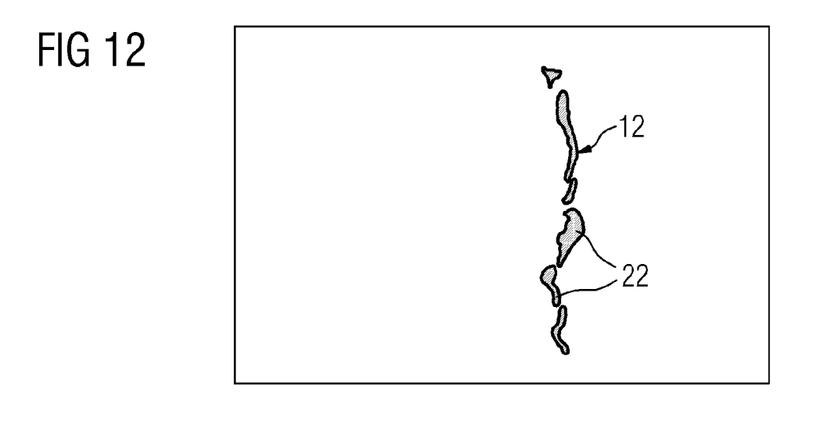
FIG. 12 shows the abnormality chart highlighting the putative crack extracted from the sub-image from FIG. 8.

The pixel union over all suspect blob clusters 24 identified in V1.7.6 yields an abnormality chart displaying all putative cracks 12 (or other wanted surface defects, if applicable, which are not considered in this example) detected in the sub-image submitted to V1.7. FIG. 12 shows a highlighting image of the crack 12 which can be obtained by image processing from the adjacency graphs, shown in FIG. 11 as example.

A detection failure of cracks would be both likely and typical for single image evaluations, which is the reason for having taken several photographs of the same region of interest under varying illumination, and for having created even more sub-images of that region in V.1.6 by pixel fusion.

V2 Fusion of Each n+q Abnormality Charts to Yield r Joint Abnormality Charts of the Tile The n+q abnormality charts of one and the same region of interest, as obtained from repeated application of V1.7 to all of the n+q sub-images available after V1.6, are merged to one joint abnormality chart of that region by setting all pixels of all n+q single abnormality charts as foreground pixels of a new binary image, and setting all remaining pixels of the region as background pixels.

Figure 13:
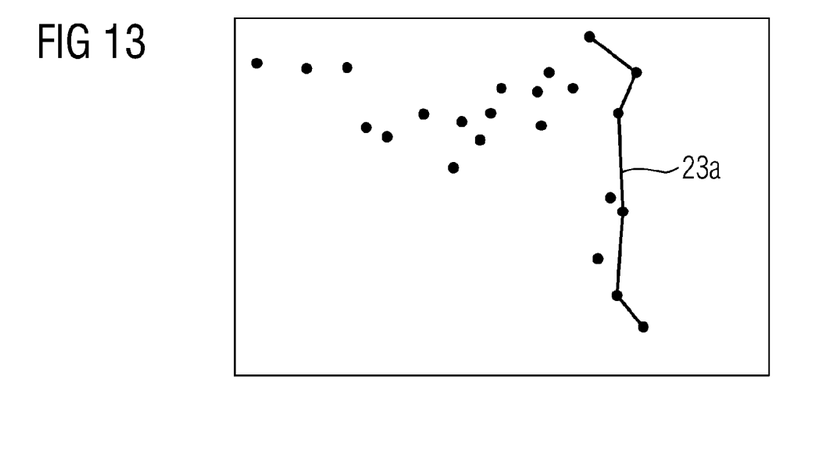
FIG. 13 shows the embedding of the adjacency graph of the joint abnormality chart generated by fusion of all single abnormality charts of all sub-images, including the abnormality chart from FIG. 12.
Figure 14:
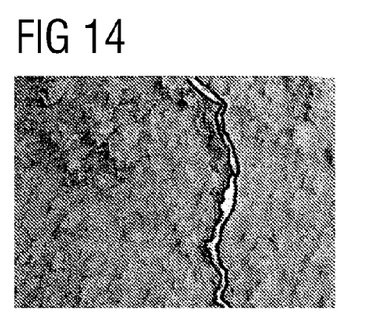
FIG. 14 shows an example of a final detection map wherein the crack is highlighted brightly.

V3 Detection of Crack-Like Texture Anomalies in Each of the r Joint Abnormality Charts The joint abnormality charts of each of the r regions of interest are resubmitted to steps V1.7.2 to V1.7.7 for finally detecting and marking suspect features in the respective surface texture. Thereby, the accept/reject bounds for the blob parameters (or, more generally, the classification function) in V1.7.6 can be different from the single image evaluation pass, taking into account the higher significance of pixels in the joint abnormality chart, as compared to the single sub-images. It is advantageous, however, to leave the distance function (in V1.7.4) and the definition of the adjacency matrix (in V1.7.5) unaltered. The adjacency graph resulting from the joint abnormality chart is shown in FIG. 13. The final pass of V1.7.7 yields the final detection map of that region of interest, displaying all putative cracks (or other wanted surface defects, if applicable) found by the algorithm V. FIG. 14 shows such a final detection map of the region around the crack 12 by bright highlighting in the corresponding sub-image. Unambiguous detection of all cracks, without mistakes, was achieved, as well as in a suite of other relevant test examples.

V4 Discrimination of False Detection Items Based on a Priori Information

In some cases, harmless features of the surface structure (in this example: not cracks) are accidentally reported by the algorithm V as a matter of false alarm. In some of these cases not even refined geometrical tests are likely to enable automatic elimination of the false classification. On the other hand, very small and thin cracks (like 5 mm long) have been detected on 20 cm large, dirty and worn tiles so that one or another false detection appears tolerable.

In other cases, false detections are easily recognized as such. E.g., the geometrical proportions of the constituting blobs may clearly indicate that the respective cluster is not a crack. Here, an a posteriori geometrical analysis will eliminate the mistaken classification.

In summary, from eight cracks (one of which has been considered in this example) prevailing in three combustion chamber tiles with rather different surface roughness none was overseen, and only one complicated false positive result was returned (together with two correct findings in the same region of interest).

W1.7 (Instead of V1.7) Alternative for the Detection of Texture Anomalies in Each of the (n+q)×r Sub-Images In contrast to V1.7.4 no assumption is made concerning the geometrical or topological structure of a defect, but anything deviating significantly from the vast majority of prevailing structural patterns is reported as an anomaly. Like V1.7 this approach works best on appropriately normalized sub-images. Unlike the above outlined implementation of V1.7, it is not tailored to finding cracks in wall tiles of turbine combustion chambers, but is kept rather general in order to efficiently complement V1.7. Any tailoring to specific defect signatures is possible, however, by appropriate concretization of the observable parameters in W1.7.2.

W1.7.1 Tiling of a Sub-Image into Partially Overlapping Chips (or Tiles)

The submitted sub-image is completely partitioned into much smaller sub-images called chips or tiles forming a parquet. These chips have all the same shape and size which is larger than the average feature size determined in V1.5. It is advantageous if adjacent chips overlap to some extent which must not vary across the parquet. The chips can be squares overlapping to 50% in either direction.

W1.7.2 Calculation of Chip Properties Relevant for their Classification

A set of characteristic parameters for the description of the chips is chosen such that chips containing structural anomalies will yield abnormal values for at least some of these parameters. Tailoring to specific anomalies is possible by according choice or design of these parameters. The success of the method W depends most on the appropriate choice of the characteristic parameters. A very general, though suitable, choice is the pair of (i) the average brightness and (ii) the peak value of the autocorrelation function inside the chip.

W1.7.3 Data Matrix of the Chips

Figure 15:
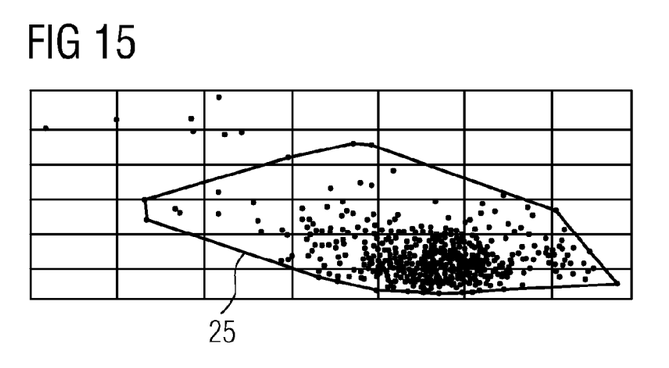

The chosen parameters are calculated for all chips, yielding a rectangular data matrix with as many data lines as the parquet contains chips, and with one column per parameter. Each data line (thus, each chip) is associated with a data point in the space of characteristic parameters. In the above example the parameter space is a plane spanned by the average brightness on the abscissa and the autocorrelation peak value on the ordinate. In this plane all chips are represented by points, as shown in FIG. 15.

W1.7.4 Detection of Outliers (Supplementary Data Points)

The set of data points is submitted to an outlier detection procedure. Generally, the procedure performs a partitioning cluster analysis with a priori unknown class number under the constraint that one class contains significantly more data points than the union of all other classes. What distance function is used depends completely on the definition of the characteristic parameters spanning the data space and has, like in V1.7.4, the by far most important influence on the quality of the outlier classification. In case of the above example, both parameters have the same dimension and order of magnitude (due to the normalization V1.3) so that, e.g., the (squared) Euclidian distance is suited. The resulting partition of the data set is shown in FIG. 15 by the line 25 circumfering all data points considered normal. The data points outside the line do not belong to that class and are considered supplementary, i.e. outliers. If the partition yields more than two classes, all but the largest class are unified to a set of supplementary data points. If the partition yields one class only, the supplementary data point set is empty.

W1.7.5 Assignment of Abnormal Chips to Outliers

All chips corresponding to supplementary data points are considered abnormal.

W1.7.6 Abnormality Chart Displaying Putative Anomalies

Figure 16:
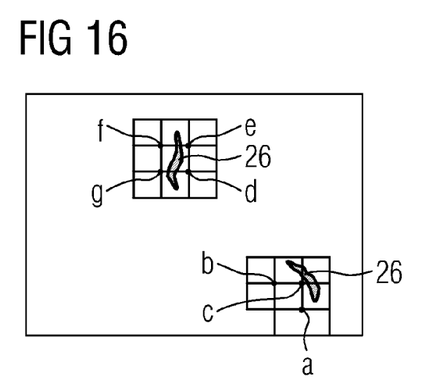

The set of abnormal chips yields the abnormality chart corresponding to the submitted image. The abnormality chart corresponding to FIG. 15 is schematically shown in FIG. 16 where the seven data points outside the line 25 in FIG. 15 have been translated back to their corresponding chips.

W3 Detection of Texture Anomalies in Each of the r Joint Abnormality Charts

The union of the n+q abnormality charts of one and the same region of interest, as obtained from repeated application of W1.7 to all of the n+q sub-images available after V1.6, is the joint abnormality chart of that region. The identification of specific defect patterns, as well as the elimination of reported, harmless features is to some extent possible by geometrical analysis.

Figure 17:
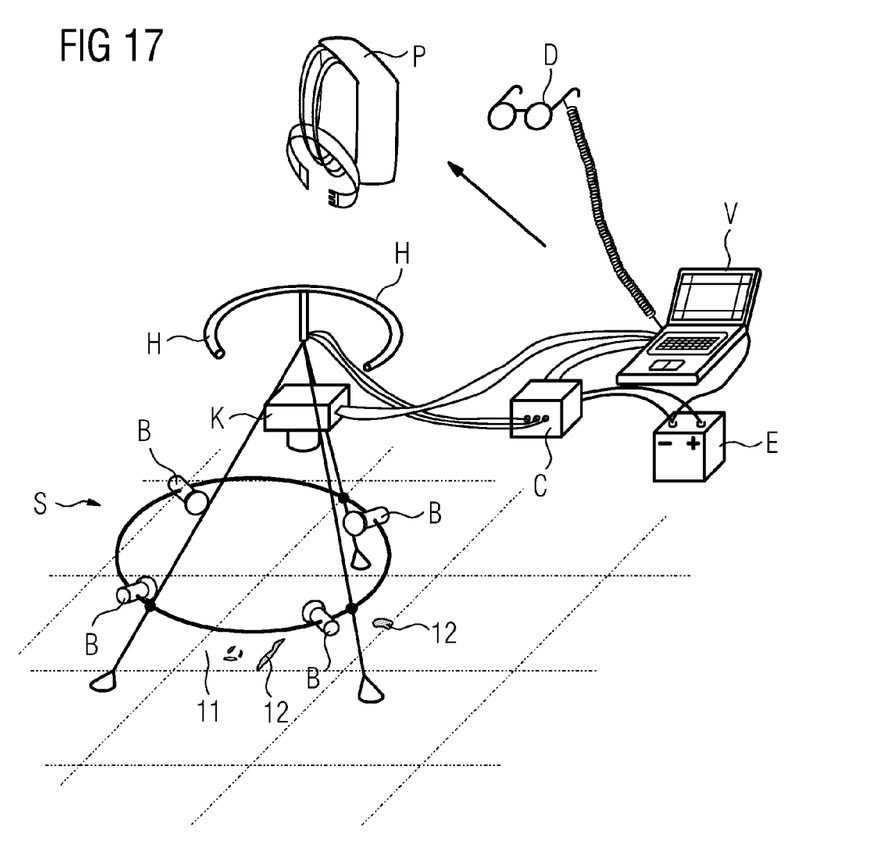
FIG. 17 shows an example for the inventive apparatus with four independent light sources.

FIG. 17 shows an example of an apparatus for the inspection of the wall tile 11 to find cracks 12 in a schematic perspective view. The apparatus comprises a support frame realized as a tripod. The support frame S can be held by an operator on handles H and positioned above the wall tile 11. On the support frame S a digital camera K and four light sources B are fixed in a position such that they are oriented towards the wall tile 11 to be inspected.

The method is controlled by a computer V which has a signal connection to the digital camera K and to a controller C. The controller C is able to drive the light sources B separately, so that the wall tile 11 can be illuminated from four different directions and each of these illumination conditions can be documented by the digital camera K.

For the portable application of the method according to various embodiments the controller C and the computer V can be driven by an energy source E. The controlling unit comprising the controller C, the energy source E and the computer V can be integrated in a back pack P. Furthermore, the operator can obtain information by wearing display spectacles.

What is claimed is:

1. A method for the optical inspection of a matt surface of an object, the surface having a random texture, for the purpose of finding texture anomalies, the method comprising at least the following main steps:

creating in a first main step n>1 digital images of the surface by an image sensor whereby the surface is illuminated from one direction for each image to be created whereby the directions for each image differ from each other, defining in a second main step r>0 regions of interest of the surface whereby all regions of interest are entirely included in the n images and a matrix of n.times.r sub-images, which consist of the r regions of interest for each of the n images, is created, independently detecting in a third main step texture anomalies in the sub-images by digital image processing and generating an abnormality charts showing the putative anomalies for each sub image, generating in a fourth main step for each of the r regions of interest a joint abnormality chart is by fusion of the n abnormality charts of said region of interest, and detecting in a fifth main step texture anomalies in each of the r joint abnormality charts.

2. The method according to claim 1, wherein in an intermediate step brightness gradients in the n images or in the n.times.r sub-images resulting from the unidirectional illumination are eliminated by an individual photometric normalization of each of said images or sub-images, respectively, before the third main step.

3. The method according to claim 1, wherein in an intermediate step surfaces appearing in the n images or in the sub-images with curved boundaries are transformed to shapes with straight or circular boundaries by an individual geometric normalization before the third main step.

4. The method according to claim 1, wherein the third main step comprises the following steps in a first step a binary sub-image is created whereby connected pixels of the sub-image with at least one of a brightness, hue, and saturation below or above a certain threshold are grouped into blobs, in a second step the blobs are analyzed with respect to at least one of their size, their position on the surface, and their spatial relation to each other.

5. The method according to claim 4, wherein the second step is performed by a selection of relevant blobs which are defined by a minimal size, by a calculation of the distance matrix of the blobs and by a partition of the blobs based on their distances to find clusters of relevant blobs supposed to represent anomalies of interest.

6. The method according to claim 5, wherein the anomalies to be found are cracks whereby linear, un-branched, open chains of relevant blobs are considered suspect.

7. The method according to claim 1, wherein there are calculated by pixel fusion all $q=n(n-1)/2$ possible sums of two out of the n images to generate q additional images before the second main step or all $q.times.r$ possible sums of two out of the n sub-images belonging to the same region of interest to generate $q.times.r$ additional sub-images for each region of interest before the third main step and the q additional images, or the $q.times.r$ additional sub-images, are treated identically as the n images or the $n.times.r$ sub-images in all subsequent steps.

8. A system for the optical inspection of a matt surface of an object, the surface having a random texture, for the purpose of finding texture anomalies, the system comprising:
 an image sensor creating n>1 digital images of the surface
 a light source illuminating the surface from one direction for each image to be created and wherein the directions for each image differ from each other, and
 processing means operable to define r>0 regions of interest of the surface wherein all regions of interest are entirely included in the n images and for creating a matrix of $n.times.r$ sub-images, which consist of the r regions of interest for each of the n images, to independently detect texture anomalies in the sub-images and to generate an abnormality charts showing the putative anomalies for each sub image, to generate for each of the r regions of interest a joint abnormality chart by fusion of the n abnormality charts of said region of interest, and to detect texture anomalies in each of the r joint abnormality charts.

9. The system according to claim 8, wherein the processing means are further operable to eliminate brightness gradients in the n images or in the $n.times.r$ sub-images resulting from the unidirectional illumination by an individual photometric normalization of each of said images or sub-images, respectively.

10. The system according to claim 8, wherein the processing means are further operable to transform surfaces appearing in the n images or in the sub-images with curved boundaries to shapes with straight or circular boundaries by an individual geometric normalization.

11. The system according to claim 8, wherein the processing means are further operable to create a binary sub-image wherein connected pixels of the sub-image with at least one of a brightness, hue, and saturation below or above a certain threshold are grouped into blobs, to analyze the blobs with respect to at least one of their size, their position on the surface, and their spatial relation to each other.

12. The system according to claim 11, wherein analyzing the blobs is performed by a selection of relevant blobs which are defined by a minimal size, by, a calculation of the distance matrix of the blobs and by a partition of the blobs based on their distances to find clusters of relevant blobs supposed to represent anomalies of interest.

13. The system according to claim 12, wherein the anomalies to be found are cracks whereby linear, un-branched, open chains of relevant blobs are considered suspect.

14. The system according to claim 8, wherein there are calculated by pixel fusion all $q=n(n-1)/2$ possible sums of two out of the n images to generate q additional images before the second main step or all $q.times.r$ possible sums of two out of the n sub-images belonging to the same region of interest to generate $q.times.r$ additional sub-images for each region of interest before the third main step and the q additional images, or the $q.times.r$ additional sub-images, are treated identically as the n images or the $n.times.r$ sub-images.

\* \* \* \* \*